United States Patent [19]

Greensite

[11] 4,121,576
[45] Oct. 24, 1978

[54] METHOD AND APPARATUS FOR PROCESSING VECTORCARDIOGRAPHIC SIGNALS FOR ENABLING QUANTITATIVE DETERMINATION OF THE PERCENTAGE OF HEART MUSCLE TISSUE AFFECTED BY AN INTERVENTION

[76] Inventor: Fred Samuel Greensite, 122 - 24th St., Del Mar, Calif. 92014

[21] Appl. No.: 766,932

[22] Filed: Feb. 9, 1977

[51] Int. Cl.$^2$ .............................................. A61B 5/04
[52] U.S. Cl. .............................................. 128/2.06 V
[58] Field of Search ....................... 128/2.06 R, 2.06 V

[56] References Cited

U.S. PATENT DOCUMENTS 3,548,813  12/1970  Berner ............................ 128/2.06 V

OTHER PUBLICATIONS

Lamb, "Vectorcardiography", 1965, only pp. 145, 162 and 163 available.
Mori et al., "Japanese Journal of Medical Electronics and Bio-Medical Engineering", vol. 13, No. 2, Apr. 1975, pp. 85-92.
Hellerstein et al., "American Journal of Cardiology", Dec. 1960, pp. 1049-1061.

Mori et al., "Japanese Circulation Journal", vol. 32, Feb. 1968, pp. 149-160.
Lamb, "American Journal of Cardiology", Jun. 1959, pp. 766-775.

Primary Examiner—William E. Kamm
Attorney, Agent, or Firm—Brown & Martin

[57] ABSTRACT

Vector cardiogram signals are processed by an analog computer circuit during a QRS wave interval in which a sheet of depolarization traverses a heart muscle to provide signals which enable a determination of the relative volume of heart muscle tissue that is functioning during the QRS wave interval. By comparing such relative volumes determined from signals processed from vectorcardiograms produced both before and after an "intervention" affecting the heart muscle, such as either a myocardial infarction or a therapeutic intervention following a myocardial infarction, it is possible to make a quantitative determination of the percentage of heart muscle tissue affected by the intervention.

A signal proportional to the volume of heart muscle tissue affected by a myocardial infarction is provided by processing vectorcardiogram signals obtained during a QRS wave interval prior to or at the onset of the infarction and vectorcardiogram signals obtained during a QRS wave interval following the infarction.

13 Claims, 9 Drawing Figures

METHOD AND APPARATUS FOR PROCESSING VECTORCARDIOGRAPHIC SIGNALS FOR ENABLING QUANTITATIVE DETERMINATION OF THE PERCENTAGE OF HEART MUSCLE TISSUE AFFECTED BY AN INTERVENTION

BACKGROUND OF THE INVENTION

The present invention generally pertains to measurement of physiological properties and is particularly directed to a method and system of electrocardiographic signal processing.

It is known that a myocardial infarction decreases the quantity of functioning tissue in the heart muscle. It is also known that a therapeutic intervention following a myocardial infarction causes a portion of the tissue in the heart muscle rendered non-functioning by the infarction to again function and thereby prevent such restored tissue from dying.

It is one object of the present invention to provide means for ascertaining the percentage of heart muscle tissue affected by an intervention. The term "intervention" when used by itself herein, refers to either a myocardial infarction or a therapeutic intervention.

It is a further object of the present invention to provide novel apparatus for electrocardiographic signal processing.

Measurements related to the functioning of the heart muscle typically are made by electrocardiographic techniques. Such electrocardiographic techniques such as vectorcardiogram signal processing are used in diagnosing myocardial infarctions. The vectorcardiogram approach is premised on an assumption that upon each contraction of the heart muscle, a sheet of electrical depolarization traverses the heart muscle, thereby providing detectable changes in electrical potential. Through the use of electrodes attached to the body, vectorcardiogram signals $x(t)$, $y(t)$, and $z(t)$, hereinafter referred to as X, Y and Z, are provided. The vectorcardiogram signals are representative of the electrical potential on the surface of the body produced by the transversal of the depolarization sheet within the heart muscle. Through the use of an analog computer vectorcardiograms have been produced and analyzed. The spatial magnitude vector cardiogram $\sqrt{X^2 + Y^2 + Z^2}$ and the spatial velocity vectorcardiogram $\sqrt{\dot{X}^2 + \dot{Y}^2 + \dot{Z}^2}$, have been studied in relation to the effects of a myocardial infarction. $\dot{X}$, $\dot{Y}$, and $\dot{Z}$ are the first derivatives with respect to time of X, Y, and Z respectively. However, such studies have not so defined that relationship as to be able to make a quantitative determination of the proporation of heart muscle tissue affected by an intervention.

SUMMARY OF THE INVENTION

The present invention provides a method of determining the proportion of heart muscle tissue affected by an intervention and apparatus for providing an indication for enabling such determination.

The proportion of tissue affected by the intervention is determined by relating the relative volume of heart muscle tissue functioning during a QRS wave interval before the intervention to the relative volume of heart muscle tissue functioning during a QRS wave interval after the intervention. Thus measurements from which the relative functioning volume determination is made must be taken both before and after the intervention.

In one preferred embodiment of the present invention, the relative volume of heart muscle tissue that is functioning during a QRS wave interval in which a sheet of depolarization traverses a heart muscle, is determined by processing vectorcardiogram signals X, Y, and Z to provide a first signal that is proportional to the product of the area of the depolarization sheet as a function of time. Preferably the first signal is provided by processing the vector cardiogram signals in an analog computer to provide a signal approximating $\sqrt{(\dot{X}^2 + \dot{Y}^2 + \dot{Z}^2)/(X^2 + Y^2 + Z^2)}$, where X, Y, and Z are the vectorcardiogram signals as a function of time.

The first signal may be further processed to provide a second signal related to the volume of heart muscle tissue that is functioning during the QRS wave interval. Preferably the second signal is provided by processing the first signal in an analog computer to provide a signal approximating $\int_{QRS} \sqrt{(\dot{X}^2 + \dot{Y}^2 + \dot{Z}^2)/(X^2 + Y^2 + Z^2)}\, dt$.

The second signal may then be further processed to provide a third signal which is proportional to the volume of heart muscle tissue that is functioning during the QRS wave interval. Prefeably this is accomplished by using an analog computer to divide the second signal by elasped time during the QRS wave interval. The third signal provided by the analog computer thus approximates $1/QRS \int_{QRS} \sqrt{(\dot{X}^2 + \dot{Y}^2 + \dot{Z}^2)/(X^2 + Y^2 + Z^2)}\, dt$.

The third signals obtained both before and after the intervention may be related to one another to determine the percentage of heart muscle tissue that is affected by the intervention.

In another preferred embodiment of the present invention, the relative volume of functioning heart muscle tissue is determined by processing the vectorcardiogram signals X, Y, and Z during a QRS wave interval to provide a first signal waveform approximating $\int_{QRS} \sqrt{\dot{X}^2 + \dot{Y}^2 + \dot{Z}^2}\, dt$; a second signal waveform approximating $\sqrt{X^2 + Y^2 + Z^2}$; and a third signal waveform approximating $\sqrt{\dot{X}^2 + \dot{Y}^2 + \dot{Z}^2}$. The relative volume of heart muscle tissue functioning during the QRS interval is determined by dividing the peak value of the first signal waveform by the product of the peak value of the second signal waveform and the duration of the QRS interval in the third signal waveform.

The apparatus of the present invention is believed to have additional utility beyond that of enabling a quantitative determination of the effect of an intervention. For example the first signal approximating $\sqrt{(\dot{X}^2 + \dot{Y}^2 + \dot{Z}^2)/(X^2 + Y^2 + Z^2)}$ produced by the apparatus is also useful in identifying the site of the infarction within the heart muscle. This first signal is proportional to the product of the area of the depolarization sheet as it traverses the heart muscle and the average curvature of the depolarization sheet as a function of time. This first signal can be expected to have a characteristic appearance in various disease states, which, when combined with the knowledge of what this signal represents physically, should lead to additional insights in various areas. The following is a list of some additional areas for investigation:

1. further classification and distinction between electrocardiographic entities such as pre-excitation syndromes and sites of arrhythmia generation;
2. distinguishing ischemic from non-ischemic changes in borderline exercise tests;
3. further distinction of pericarditis from infarction; and 4. as an easily readable screening test for cardiac disease.

Some of the significant advantages of the present invention are as follows. It enables immediate measurement of the quantitative effect of a therapeutic intervention. It enables a quantitative measurement of the magnitude of the effect of a myocardial infarction. It is applicable to measuring the effect of infarctions at any location within the heart, including small subendocardial infarctions. It requires the use of only four peripheral electrodes and one back electrode to provide the vectorcardiogram signals that are processed. It is relatively inexpensive and can be applied and evaluated easily and quickly.

The present invention further provides an apparatus for providing an indication of the volume of heart muscle which is adversely affected by a myocardial infarction.

In regard to this aspect of the present invention it has been found that the volume of heart muscle tissue affected by a myocardial infarction is approximately equal to:

$$\frac{W \cdot A}{QRS \left(\sqrt{X^2 + Y^2 + Z^2}\right)_{PRE\,MAX}} \text{ times}$$

$$\int_{QRS} \sqrt{(X_{PRE} - JX_{POST})^2 + (Y_{PRE} - JY_{POST})^2 + (Z_{PRE} - JZ_{POST})^2} \, dt;$$

wherein X, Y, and Z are vectorcardiogram signals as a function of time during a QRS interval in which a sheet of depolarization traverses the heart muscle;

$$J\, 5\, msec \text{ equals } \frac{(\sqrt{X^2 + Y^2 + Z^2})5\, msec\, PRE}{(\sqrt{X^2 + Y^2 + Z^2})5\, msec\, POST};$$

"5 msec" refers either to a time five milliseconds before the end of the QRS interval in anterior and anterior-septal myocardial infarctions, or to a time five milliseconds after the beginning of the QRS interval in posterior and inferior myocardial infarctions;

W equals the width of the interventricular septum of the heart muscle;

A equals the area of the cardiac base of the heart muscle; and $(\sqrt{X^2 + Y^2 + Z^2})_{PRE\,MAX}$ is the maximum value of $\sqrt{X^2 + Y^2 + Z^2}$ during the QRS interval prior to or at the onset of the myocardial infarction.

Accordingly the apparatus of the present invention for providing an indication of the volume of heart muscle tissue which is adversely affected by a myocardial infarction, includes a memory device for storing vector cardiogram signals obtained during a QRS wave interval in which a sheet of depolarization transverse a heart muscle prior to or at the onset of the myocardial infarction, and vectorcardiogram signals obtained during a QRS wave interval in which a sheet of depolarization traverses the heart muscle following the myocardial infarction; and an arithmetic processing unit for processing the stored signals for providing a signal that is proportional to the volume of heart muscle tissue affected by the myocardial infarction. The volume proportional signal provided by the arithmetic processing unit approximates $$\int_{QRS} \sqrt{(X_{PRE} - JX_{POST})^2 + (Y_{PRE} - JY_{POST})^2 + (Z_{PRE} - JZ_{POST})^2} \, dt;$$

Although it is preferable that the "PRE" vectorcardiogram signals which are stored for processing by the arithmetic processing unit be vectorcardiogram signals that were obtained prior to the onset of the myocardial infarction, such signals are not always available. Oftentimes they have not been obtained and/or recorded. In such event "PRE" vectorcardiogram signals obtained at the onset of the myocardial infarction may nevertheless be processed in accordance with the present invention. The onset of a myocardial infarction is defined herein as within the first twelve hours after the beginning of the infarction.

The "POST" vectorcardiogram signals preferably are obtained after such time as the changes in the vectorcardiogram waveforms produced during the QRS interval have fully evolved in response to the myocardial infarction. Typically this is at least 72 hours after the beginning of the infarction.

The volume proportional integral signals provided by the arithmetic processing unit may analyzed to provide an indication of the effect of a therapeutic intervention following a myocardial infarction. The integral signal is first provided for values of (X, Y, Z)$_{POST}$ obtained before the therapeutic intervention and is secondly provided for values of (X, Y, Z)$_{POST}$ obtained after the therapeutic intervention. These first and second integral signals are then compared. A decrease in the value of the integral signal indicates that the effect of said therapeutic intervention is beneficial.

DESCRIPTION OF THE PREFERRED EMBODIMENT

Figure 1:
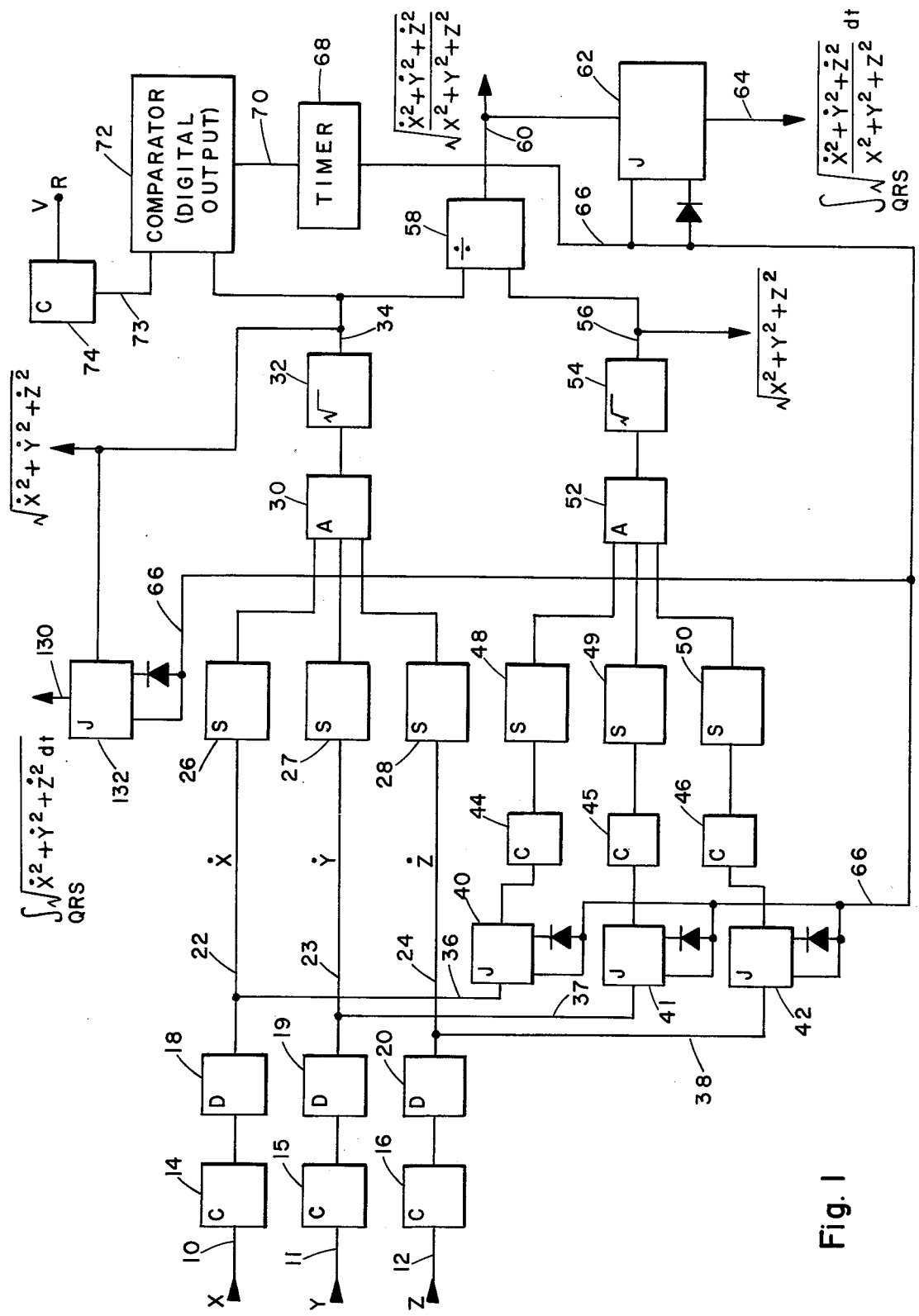
FIG. 1 is a block diagram of an analog computer circuit for processing electrocardiographic signals in accordance with the present invention.
Figure 2:
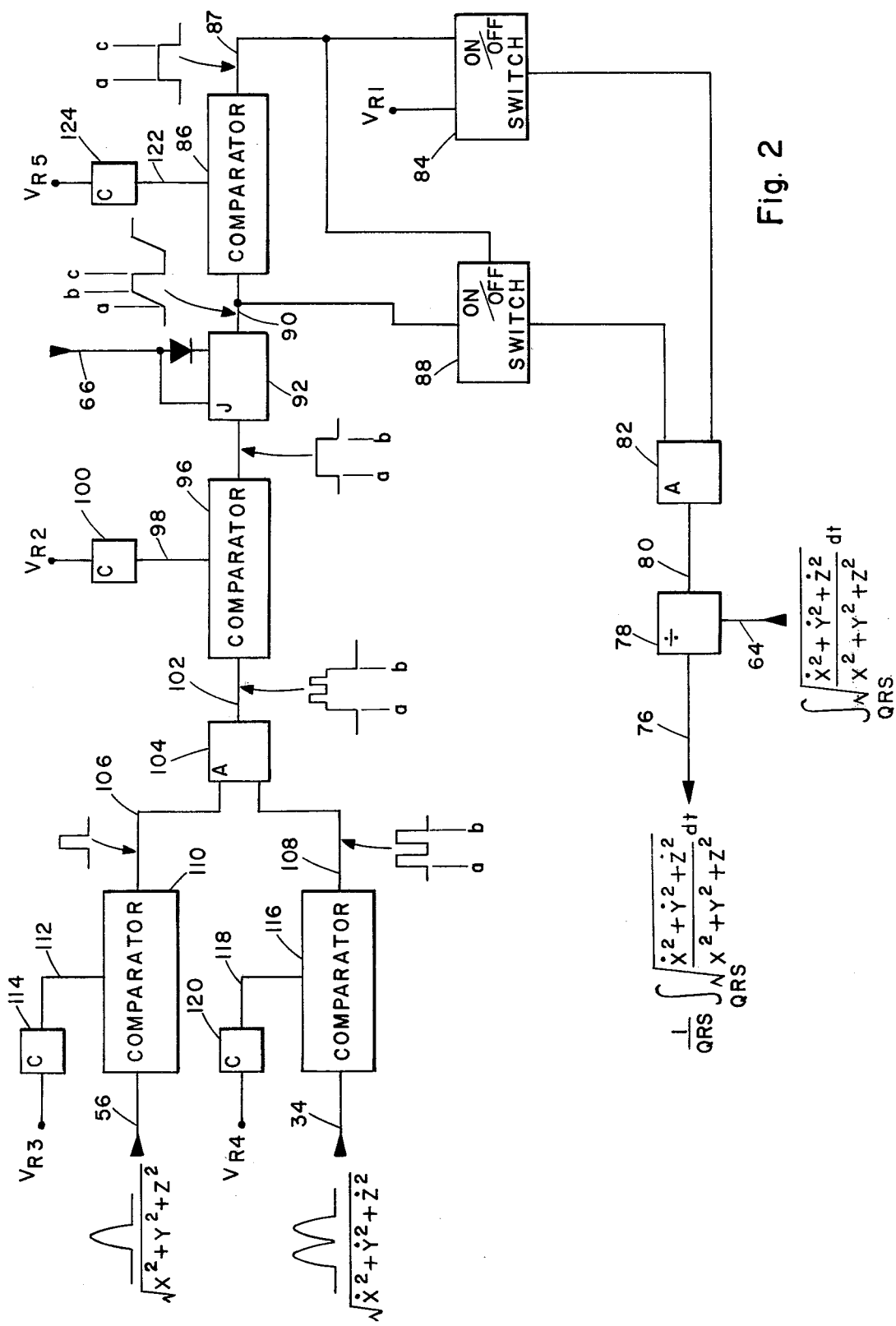
FIG. 2 is a block diagram of an analog computer circuit that is used in combination with the circuit of FIG. 1.
Figure 3A:
FIGS. 3a through 3f illustrate vectorcardiographic signal waveforms and also the signal waveforms processed therefrom in accordance with one preferred embodiment of the present invention.
Figure 3B:
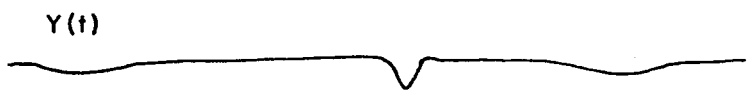
Figure 3C:
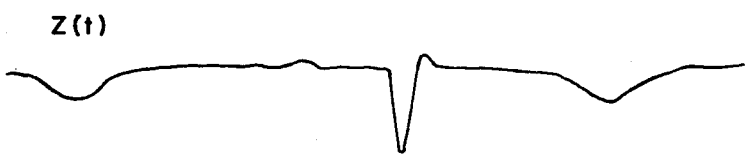

An analog computer circuit for processing vectorcardiogram signals in accordance with the present invention is shown in FIGS. 1 and 2. Vectorcardiogram signals X, Y, and Z that are produced by a standard vectorcardiograph machine (not shown) are received on input lines 10, 11, and 12 respectively. The vectorcardiogram signals may be transmitted to the processing circuit of FIGS. 1 and 2 as they are produced by the vectorcardiographic machine or they may be recorded when they are produced and subsequently reproduced for provision to lines 10, 11, and 12 of the processing circuits. The waveforms of the vectorcardiogram signals are illustrated in FIGS. 3a, 3b, and 3c as X(t), Y(t), and Z(t).

The signals X, Y, and Z are first passed through scaling constant components (identified by the symbol "C") 14, 15, and 16 in order to place their voltages within the functional tolerance of the operational amplifiers within the components of the processing circuit. The scaled signals X, Y, and Z are then differentiated by differentiator components (identified by the symbol "D") 18, 19, and 20 to produce the signals $\dot{X}$, $\dot{Y}$, and $\dot{Z}$.

The $\dot{X}$, $\dot{Y}$, and $\dot{Z}$ signals on lines 22, 23, and 24 from the differentiators 18, 19, and 20 are squared by squaring components (identified by the symbol "S") 26, 27, and 28 and combined by an adder component (identified by the symbol "A") 30. The square root of the signal from the adder 30 is provided by a square root component (identified by the symbol "√") 32 to provide the signal $\sqrt{\dot{X}^2 + \dot{Y}^2 + \dot{Z}^2}$ on line 34. This signal is the spatial velocity vectorcardiogram referred to hereinabove in the discussion of the background of the invention.

The $\dot{X}$, $\dot{Y}$, and $\dot{Z}$ signals on lines 36, 37, and 38 from the differentiators 18, 19, and 20 are integrated by integrator components 40, 41, and 42 (identified by the symbol "J") to again produce signals X, Y, and Z. The X, Y, and Z signals from the integrators 40, 41, and 42 are passed through scaling constant components 44, 45, and 46 and squaring components 48, 49, and 50, and then combined by an adder component 52. The square root of the signal from the adder 52 is provided by a square root component 54 to provide the signal $\sqrt{X^2 + Y^2 + Z^2}$ on line 56.

The signal on line 34 is divided in divider component (identified by the symbol "÷") 58 by the signal on line 56 to produce the signal $\sqrt{(\dot{X}^2 + \dot{Y}^2 + \dot{Z}^2)/(X^2 + Y^2 + Z^2)}$ on line 60. This is the "first signal", mentioned in the discussion of the first preferred embodiment referred to in the "Summary of the Invention" hereinabove, that is proportional to the product of the area of the depolarization sheet and the average curvature of the depolarization sheet as a function of time.

The "first signal" on line 60 is integrated by the integrator component 62 to provide the "second signal" $QRS \sqrt{(\dot{X}^2 + \dot{Y}^2 + \dot{Z}^2)/(X^2 + Y^2 + Z^2)} \, dt$ on line 64. In order to provide such an integral signal over the QRS interval it is necessary that a timing signal be provided on line 66 from a timer 68 to the integrator 62. The timing signal on line 66 is also provided to the other integrator components shown in FIGS. 1 and 2. The duration of the timing signal provided is at least 90 milliseconds so as to extend beyond the duration of the QRS interval.

The timer 68 provides a signal on line 66 during the interval that a digital output signal of a given binary state is produced on line 70 from a comparator 72. Since such a digital signal should be provided only during the QRS interval, the amplitude of the signal $\sqrt{\dot{X}^2 + \dot{Y}^2 + \dot{Z}^2}$ on line 34, which is significant only during the QRS interval is compared with a reference signal on line 73 provided by a scaling constant component 74 from a reference voltage source $V_R$; and the timer 68 is enabled by the digital signal on line 70 from the comparator 72 only while the amplitude of the signal on line 34 exceeds the amplitude of the reference signal on line 73.

Referring to FIG. 2, the "third signal" $1/QRS \, QRS \sqrt{(\dot{X}^2 + \dot{Y}^2 + \dot{Z}^2)/(X^2 + Y^2 + Z^2)} \, dt$, which is proportional to the volume of heart muscle tissue that is functioning during the QRS interval, is provided on line 76 from a divider component 78, which divides the signal on line 64 by the signal on line 80. The signal on line 80 represents the quantity QRS, "QRS" being the duration of the QRS interval. However, since the divider component 78 is not functionally accurate when dividing by a signal having an amplitude outside of a given tolerance, such as when the QRS duration is very close to zero, it is necessary that at the beginning of the QRS interval, a signal having a low constant amplitude within the tolerance of the divider 78 be provided on line 80. Such a low constant amplitude signal is provided on line 80 via an adder component 82 from a voltage reference source $V_{R1}$ when the switch 84 is switched on in response to a signal on line 87 from the comparator 86 while the duration QRS is very close to zero. When the duration QRS is no longer close to zero, the state of the signal on line 87 from the comparator 86 changes to turn off the switch 84 and turn on the switch 88 so as to provide to the adder 82 only the signal on line 90 from the output of the integrator component 92.

The signal on line 90 has a constantly rising slope during the QRS wave interval, thereby providing a signal that is proportional to the duration QRS. The signal having a constantly rising slope is provided on line 90 by the integrator 92 during the interval "a" to "b" of the square wave signal on line 94. The square wave signal on line 94 is produced by the comparator 96 during the QRS interval as determined by comparing a reference signal provided on line 98 from voltage reference source $V_{R2}$ via a scaling constant component 100, with a signal provided on line 102 from an adder component 104.

The adder 104 combines the signals on lines 106 and 108. The signal on line 106 is produced by the comparator 110 when the amplitude of the signal $\sqrt{X^2 + Y^2 + Z^2}$ on line 56 exceeds the amplitude of a reference signal provided on line 112 from a voltage reference source $V_{R3}$ via a scaling constant component 114. The signal on line 108 is produced by the comparator 116 when the amplitude of the signal $\sqrt{\dot{X}^2 + \dot{Y}^2 + \dot{Z}^2}$ on line 34 exceeds the amplitude of a reference signal provided on line 118 from a voltage reference source $V_{R4}$ via a scaling constant component 120.

Although the duration of the signal on line 34 is the QRS duration, the amplitude of the signal on line 34 may drop sufficiently close to zero between its two peaks during the QRS wave of a certain individual's heart beat (as shown in FIG. 2), that a square wave of sufficient magnitude for integration by the integrator 92 to produce a signal of constantly rising slope during the QRS duration "a" to "b" would not be provided by comparing only the signal on line 34 with a reference signal. Thus it is preferred to combine the signal from line 34 with the signal from line 56 which has a peak between the two peaks of the signal on line 34. After the signal on line 90 has stopped rising at time "b" it remains constant until the expiration of the timing signal on line 66 at time "c".

The signal on line 87 from the comparator 86 does not change states to switch off switch 84 and switch on switch 88 until the amplitude of the signal on line 90 has risen by an amount sufficient to exceed the amplitude of a reference signal provided on line 122 from a reference voltage source $V_{R5}$ via a scaling constant component 124.

The processing circuit also provides an output signal $QRS \sqrt{\dot{X}^2 + \dot{Y}^2 + \dot{Z}^2} \, dt$ on line 130 from an integrator component 132. The signal on line 130 is proportional to the arc length of the vectorcardiograph loop during the QRS interval.

In an alternative preferred embodiment of the present invention utilizing appropriate portions of the circuit shown in FIG. 1, the vectorcardiogram signals X, Y, and Z are processed to provide a first signal waveform approximating $QRS \sqrt{\dot{X}^2 + \dot{Y}^2 + \dot{Z}^2} dt$; a second signal waveform approximating $\sqrt{X^2 + Y^2 + Z^2}$; and a third signal waveform approximating $\sqrt{\dot{X}^2 + \dot{Y}^2 + \dot{Z}^2}$.

The first, second and third signal waveforms as provided by display apparatus (not shown) connected to lines 130, 56 and 34 respectively. The display apparatus preferably is a strip chart recorder, although an oscilloscope may also be used either in combination with the strip chart recorder or separately.

Figure 3D:
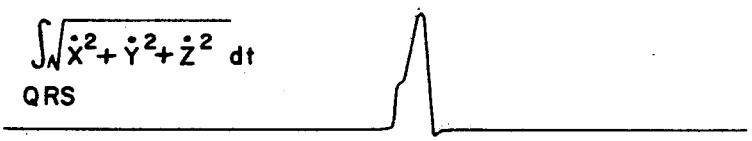
Figure 3E:
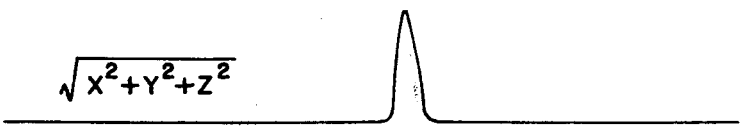
Figure 3F:

Examples of the first, second and third signal waveforms are illustrated in FIGS. 3d, 3e, and 3f respectively. These waveform signals were provided by processing the vectorcardogram signals X, Y, and Z illustrated in FIGS. 3a, 3b, and 3c respectively.

The relative volume of heart muscle tissue functioning during a QRS interval is determined by dividing the peak value of the first signal waveform (FIG. 3d) by the product of the peak value of the second signal waveform (FIG. 3e) and the duration of the QRS interval in the third signal waveform (FIG. 3f).

This alternative embodiment of the present invention has been tested in experiments with laboratory animals and has been observed to be reasonably accurate.

The percentage of heart muscle affected by an intervention is calculated in accordance with the following formula:

$$100 - 100 [\text{Volume}_{POST}/\text{Volume}_{PRE}],$$

wherein Volume $_{POST}$ is the relative volume of heart muscle tissue functioning during a QRS wave interval after the intervention and Volume $_{PRE}$ is the relative volume of heart muscle tissue functioning during a QRS wave interval before the intervention.

Figure 4:
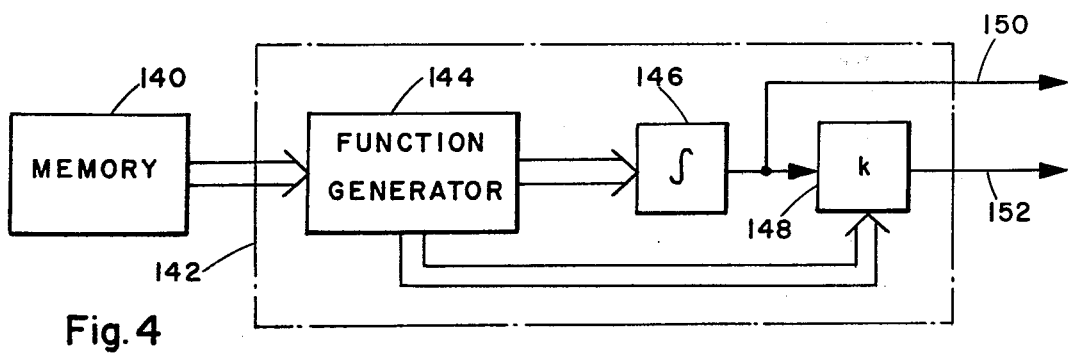
FIG. 4 is a block diagram of an apparatus for providing an indication of the volume of heart muscle which is adversely affected by a myocardial infarction.

Referring to FIG. 4, the apparatus for providing an indication of the volume of heart muscle tissue which is adversely affected by a myocardial infarction includes a memory 140 and an arithmetic processing unit 142. The arithmetic processing unit includes a function generator 144 an integrator 146 and a constant multiplier 148. The memory 140 and arithmetic processing unit 142 include typical digital computer data processing elements.

Vectorcardigram signals (X, Y, Z)$_{PRE}$ obtained during a QRS wave interval in which a sheet of depolarization traverses a heart muscle prior to or at the onset of the myocardial infarction and vectorcardiogram signals (X, Y, Z)$_{POST}$ obtained during a QRS wave interval in which a sheet of depolorization traverses said heart muscle following the myocardial infarction are stored in the memory 140.

The function generator 144 draws upon the signals stored in the memory to provide both the function:

$$\sqrt{(X_{PRE} - JX_{POST})^2 + (Y_{PRE} - JY_{POST})^2 + (Z_{PRE} - JZ_{POST})^2};$$

and the timing of the QRS interval to the integrator 146.

The QRS interval timing is derived from the vectorcardiogram signals obtained prior to or at the onset of the myocardial infarction.

The integrator 146 provides the volume proportional integral signal:

$$QRS \sqrt{(X_{PRE} - JX_{POST})^2 + (Y_{PRE} - JY_{POST})^2 + (Z_{PRE} - JZ_{POST})^2} dt;$$

on line 150, and also provides such signal to the constant multiplier 148. The constant multiplier 148 multiplies the volume proportional integral signal by the following quantity $$\frac{W \cdot A}{QRS (\sqrt{X^2 + Y^2 + Z^2})_{PRE \, MAX}},$$

to provide a signal on line 152 approximating the volume of heart muscle tissue affected by myocardial infarction. The quantity "W" which equals the width of the interventricular septum of the heart muscle is obtained by ultrasonic measurements and is preset in the multiplier 148. The quantity "A", which equals the area of the cardiac base of the heart muscle is obtained by chest X-ray and also is preset in the multiplier 148. The quantity "QRS" is obtained from the function generator 144. Preferably the quantity QRS is computed by the function generator 144 in essentially the same manner as by the analog computer circuit shown in FIG. 2. The quantity $(\sqrt{X^2 + Y^2 + Z^2})$PRE MAX which is the maximum value of $\sqrt{X^2 + Y^2 + Z^2}$ during the QRS interval prior to or at the onset of the myocardial infarction, is provided by the function generator 144.

I claim:

1. A method of determining the percentage of heart muscle tissue affected by an intervention, comprising both before and after intervention,
   receiving vectorcardiogram signals during a QRS wave interval in which a sheet of depolarization traverses a heart muscle, and
   processing said vectorcardiogram signals to determine the relative volume of heart muscle tissue functioning during said QRS wave interval; and
   relating the relative volumes determined both before and after said intervention;
   wherein the processing step comprises
   providing a first signal proportional to the product of the area of the depolarization sheet and the average curvature of the depolarization sheet as a function of time, in response to said vectorcardiogram signals;
   providing a second signal related to the volume of heart muscle tissue functioning during said QRS interval, in response to the said first signal; and
   providing a third signal proportional to the volume of heart muscle tissue functioning during said QRS interval, in response to said second signal.

2. A method of determining the percentage of heart muscle tissue affected by an intervention, comprising both before and after said intervention,
   receiving vectorcardiogram signals during a QRS wave interval in which a sheet of depolarization traverses a heart muscle, and
   processing said vectorcardiogram signals to determine the relative volume of heart muscle tissue functioning during said QRS wave interval; and
   relating the relative volumes determined both before and after said intervention;
   wherein the processing step comprises
   providing a signal approximating $\sqrt{(\dot{X}^2 + \dot{Y}^2 + \dot{Z}^2)/(X^2 + Y^2 + Z^2)}$ wherein X, Y, and Z are said vectorcardiogram signals as a function to time;
    providing a second signal related to the volume of heart muscle tissue functioning during said QRS wave interval, said second signal approximating $\int_{QRS} \sqrt{(\dot{X}^2 + \dot{Y}^2 + \dot{Z}^2)} / (X^2 + Y^2 + Z^2) \, dt$; and
    dividing said second signal by elapsed time during said QRS wave interval to provide a signal proportional to the volume of heart muscle tissue functioning during said QRS interval.

3. A method of determining the percentage of heart muscle tissue affected by an intervention, comprising;
  both before and after said intervention,
  receiving vectorcardiogram signals during a QRS wave interval in which a sheet of depolarization traverses a heart muscle; and
  processing said vectorcardiogram signals to determine the relative volume of heart muscle tissue functioning during said QRS wave interval; and
  relating the relative volumes determined both before and after said intervention;
  wherein the processing step comprises;
    providing a first signal waveform approximating $\int_{QRS} \sqrt{\dot{X}^2 + \dot{Y}^2 + \dot{Z}^2} \, dt$;
    providing a second signal waveform approximating $\sqrt{X^2 + Y^2 + Z^2}$;
    providing a third signal waveform approximating $\sqrt{\dot{X}^2 + \dot{Y}^2 + \dot{Z}^2}$;
  wherein X, Y, and Z are said vectorcardiogram signals as a function of time; and
    dividing the peak value of the first signal waveform by the product of the peak value of the second signal waveform and the duration of the QRS interval in the third signal waveform to determine the relative volume of heart muscle tissue functioning during said QRS interval.

4. Apparatus for providing an indication for enabling quantitative determination of the percentage of heart muscle tissue affected by an intervention, comprising;
  means for receiving vectorcardiogram signals during a QRS wave interval in which a sheet of depolarization traverses a heart muscle; and
  means for processing said vectorcardiogram signal to determine the relative volume of heart muscle tissue functioning during said QRS wave interval.

5. An apparatus according to claim 4, comprising;
  means responsive to said vectorcardiogram signals for providing a first signal proportional to the product of the area of the depolarization sheet and the average curvature of the depolarization sheet as a function of time.

6. Apparatus according to claim 5, further comprising;
  means responsive to said first signal for providing a second signal related to the volume of heart muscle tissue functioning during said QRS wave interval.

7. Apparatus according to claim 6, further comprising;
  means responsive to said second signal for providing a third signal proportional to the volume of heart muscle tissue functioning during said QRS wave interval.

8. Apparatus according to claim 5, wherein the means for providing said first signal comprises;
  means for providing a signal approximating $\sqrt{(\dot{X}^2 + \dot{Y}^2 + \dot{Z}^2)/(X^2 + Y^2 + Z^2)}$ where X, Y, and Z are said vectorcardiogram signals as a function of time.

9. Apparatus according to claim 8, further comprising;
  means responsive to said first signal for providing a second signal related to the volume of heart muscle tissue functioning during said QRS wave interval said means further comprising;
  means for providing a second signal approximating $\int_{QRS} \sqrt{(\dot{X}^2 + \dot{Y}^2 + \dot{Z}^2)/(X^2 + Y^2 + Z^2)} \, dt$.

10. Apparatus according to claim 9, further comprising;
  means for dividing said second signal by elapsed time during said QRS wave interval to provide a signal proportional to the volume of heart muscle tissue functioning during said QRS wave interval.

11. An apparatus according to claim 4, wherein the processing means comprises;
  means for providing a first signal waveform approximating $\int_{QRS} \sqrt{\dot{X}^2 + \dot{Y}^2 + \dot{Z}^2} \, dt$;
  means for providing a second signal waveform approximating $\sqrt{X^2 + Y^2 + Z^2}$;
  means for providing a third signal waveform approximating $\sqrt{\dot{X}^2 + \dot{Y}^2 + \dot{Z}^2}$; wherein X, Y, and Z are said vectorcardiogram signals as a function of time; and means for dividing the peak value of the first signal waveform by the product of the peak value of the second signal waveform and the duration of the QRS interval in the third signal waveform to determine the relative volume of heart muscle tissue functioning during said QRS interval.

12. Apparatus for providing an indication of the volume of heart muscle tissue which is adversely affected by a myocardial infarction, comprising
  means for storing vectorcardiogram signals obtained during a QRS wave interval in which a sheet of depolarization traverses a heart muscle prior to or at the onset of said myocardial infarction, and vectorcardiogram signals obtained during a QRS wave interval in which a sheet of depolarization traverses said heart muscle following said myocardial infarction; and
  means for processing said stored signals for providing a signal that is proportional to the volume of heart muscle tissue affected by said myocardial infarction;
  wherein said volume proportional signal provided by the processing means approximates:
$$\int_{QRS} \sqrt{(X_{PRE} - JX_{POST})^2 + (Y_{PRE} - JY_{POST})^2 + (Z_{PRE} - JZ_{POST})^2} \, dt;$$
wherein X, Y, and Z are said vectorcardiogram signals as a function of time;

$$J \text{ equals } \frac{(\sqrt{X^2 + Y^2 + Z^2})5 \text{ msec } PRE}{(\sqrt{X^2 + Y^2 + Z^2})5 \text{ msec } POST}$$

PRE and POST refer to respective vectorcardiogram signals stored prior to or at the onset, and following said myocardial infarction; and "5 msec" refers either to a time five milliseconds before the end of said QRS interval in anterior and anterior serial myocardial infarctions, or to a time five milliseconds after the beginning of said QRS interval in posterior and inferior myocardial infarctions; and wherein said processing means comprises means for multiplying said volume proportional signal by the following quantity:

$$\frac{W \cdot A}{QRS(\sqrt{X^2 + Y^2 + Z^2})_{PRE\ MAX}},$$

to provide a signal approximating the volume of heart muscle tissue affected by said myocardial infarction; wherein W equals the width of the interventricular septum of the heart muscle;

A equals the area of the cardiac base of the heart muscle; and $(\sqrt{X^2 + Y^2 + Z^2})$PRE MAX is the maximum value of $\sqrt{X^2 + Y^2 + Z^2}$ during said QRS interval prior to or at the onset of said myocardial infarction.

13. Apparatus for providing an indication for enabling quantitative determination of the effect of a therapeutic intervention following a myocardial infarction, comprising means for storing vectorcardiogram signals obtained during a QRS wave interval in which a sheet of depolarization traverses a heart muscle prior to or at the onset of said myocardial infarction, and vectorcardiogram signals obtained during QRS wave intervals in which a sheet of depolarization traverses said heart muscle following said myocardial infarction; and means for processing said stored signals to provide an integral signal approximating $_{QRS}\int \sqrt{(X_{PRE} - JX_{POST})^2 + (Y_{PRE} - JY_{POST})^2 + (Z_{PRE} - JZ_{POST})^2}\, dt$ wherein X, Y, and Z are said vectorcardiogram signals as a function of time;

$$J\ 5\ msec\ equals\ \frac{(\sqrt{X^2 + Y^2 + Z^2})5\ msec\ PRE}{(\sqrt{X^2 + Y^2 + Z^2})5\ msec\ POST};$$

PRE and POST refer to respective vectorcardiogram signals stored prior to or at the onset, and following said myocardial infarction; and "5 msec" refers either to a time five milliseconds before the end of said QRS interval in anterior and anterior-septal myocardial infarctions, or to a time five milliseconds after the beginning of said QRS interval in posterior and inferior myocardial infarctions.

* * * * *